United States Patent
Kanan et al.

(10) Patent No.: US 11,227,684 B2
(45) Date of Patent: Jan. 18, 2022

(54) SYSTEMS AND METHODS FOR PROCESSING ELECTRONIC IMAGES FOR HEALTH MONITORING AND FORECASTING

(71) Applicant: PAIGE.AI, Inc., New York, NY (US)

(72) Inventors: Christopher Kanan, Rochester, NY (US); Rodrigo Ceballos Lentini, Long Island City, NY (US); Jillian Sue, New York, NY (US); Thomas Fuchs, New York, NY (US); Leo Grady, New York, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/119,885

(22) Filed: Dec. 11, 2020

(65) Prior Publication Data
US 2021/0193301 A1    Jun. 24, 2021

Related U.S. Application Data
(63) Continuation of application No. 17/107,121, filed on Nov. 30, 2020.
(Continued)

(51) Int. Cl.
 *G16H 30/40* (2018.01)
 *G16H 50/20* (2018.01)
 *G06T 7/00* (2017.01)

(52) U.S. Cl.
 CPC .......... *G16H 30/40* (2018.01); *G06T 7/0012* (2013.01); *G16H 50/20* (2018.01); *G06T 2207/20081* (2013.01); *G06T 2207/20084* (2013.01)

(58) Field of Classification Search
 None
 See application file for complete search history.

(56) References Cited

U.S. PATENT DOCUMENTS

2016/0089089 A1 *   3/2016   Kakkar ............... A61B 5/0022
                                                  600/484
2016/0364862 A1 * 12/2016   Reicher ................... G06K 9/66
(Continued)

FOREIGN PATENT DOCUMENTS

WO       2017083568 A1    5/2017

OTHER PUBLICATIONS

Chovatiya ("Prediction of Dengue using Recurrent Neural Network", IEEE May 6, 2019, pp. 926-929) (Year: 2019).*

(Continued)

*Primary Examiner* — Wei Wen Yang
(74) *Attorney, Agent, or Firm* — Bookoff McAndrews, PLLC (57) ABSTRACT

Systems and methods are disclosed for determining at least one geographic region of a plurality of geographic regions, at least one data variable, and/or at least one health variable, estimating a current prevalence of a data variable in a geographic region of the plurality of geographic regions, determining a trend in a relationship between the data variable and the geographic region at a current time, determining a second trend in the relationship between the data variable and the geographic region at at least one prior point in time, determining if the trend in the relationship is irregular within a predetermined threshold with respect to the second trend from the at least one prior point in time, and, upon determining that the trend in the relationship is irregular within a predetermined threshold, generating an alert.

20 Claims, 9 Drawing Sheets

Related U.S. Application Data

(60) Provisional application No. 62/951,491, filed on Dec. 20, 2019.

(56) References Cited

U.S. PATENT DOCUMENTS

2019/0272925 A1    9/2019  Barrett et al.
2021/0090694 A1*   3/2021  Colley .................. G16H 50/70

OTHER PUBLICATIONS

Zhou ("Monitoring Epidemic Alert Levels by Analyzing Internet Search Volume" IEEE, Feb. 2013, pp. 446-452) (Year: 2013).*
Solomon et al., ("Mobile application for pre-screening of Ebola virus disease" IEEE, 2017, pp. 512-516) (Year: 2017).*
International Search Report and Written Opinion in International Patent Application No. PCT/US2020/063442 (13 pages, in English).

* cited by examiner

SYSTEMS AND METHODS FOR PROCESSING ELECTRONIC IMAGES FOR HEALTH MONITORING AND FORECASTING

CROSS-REFERENCE TO RELATED APPLICATION(S)

This application claims priority to U.S. application Ser. No. 17/107,121, filed on Nov. 30, 2020, which claims priority to U.S. Provisional Application No. 62/951,491 filed Dec. 20, 2019, the entire disclosures of which are hereby incorporated herein by reference in their entireties.

FIELD OF THE DISCLOSURE

Various embodiments of the present disclosure pertain generally to population health monitoring and forecasting by processing electronic images. More specifically, particular embodiments of the present disclosure relate to systems and methods for identifying or detecting patient health trends in a specific geographic region. The present disclosure further provides systems and methods for automatically detecting and forecasting population health trends based on one or more patient health variables.

BACKGROUND

Global population health monitoring is useful for monitoring the spread of existing diseases, the occurrences of new diseases, and determining if specific disease rates are changing. However, this information is hard to monitor and organize for numerous reasons, ranging from a lack of personnel, inadequate communication among hospitals, and inadequate data collection and analysis tools. Population health information is critical for agencies operating at the global, national, state and local levels to make informed decisions and to be aware of emerging threats to communities across these scales. Even when information is available, it may be flawed. Poor epidemiological information can lead to poor decision making and the misallocation of resources.

In one method, epidemiologists and other disease researchers might track an increase in a particular known disease in an area with information obtained by pathologists or other individuals associated with a diagnosis. This information collection process may be very slow and encounter substantial amounts of time lag due to the amount of information involved.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for monitoring a population health using artificial intelligence (AI).

A method for monitoring a population health using AI includes: determining at least one relationship between at least one geographic region of a plurality of geographic regions, at least one data variable, and/or at least one health variable; estimating a current prevalence of a data variable in a geographic region of the plurality of geographic region of the plurality of geographic regions; determining a trend in a relationship between the data variable and the geographic region at a current time; determining a second trend in the relationship between the data variable and the geographic region at at least one prior point in time; determining if the trend in the relationship is irregular within a predetermined threshold, generating an alert.

A system for monitoring a population health using AI includes a memory storing instructions; and at least one processor executing the instructions to perform a process including determining at least one relationship between at least one geographic region of a plurality of geographic regions, at least one data variable, and/or at least one health variable; estimating a current prevalence of a data variable, and/or at least one health variable; estimating a current prevalence of a data variable in a geographic region of the plurality of geographic region of the plurality of geographic regions; determining a trend in a relationship between the data variable and the geographic region at a current time; determining a second trend in the relationship between the data variable and the geographic region at at least one prior point in time; determining if the trend in the relationship is irregular within a predetermined threshold, generating an alert.

A non-transitory computer-readable medium storing instructions that, when executed by a processor, cause the processor to perform a method for monitoring a population health, the method including determining at least one relationship between at least one geographic region of a plurality of geographic regions, at least one data variable, and/or at least one health variable; estimating a current prevalence of a data variable, and/or at least one health variable; estimating a current prevalence of a data variable in a geographic region of the plurality of geographic region of the plurality of geographic regions; determining a trend in a relationship between the data variable and the geographic region at a current time; determining a second trend in the relationship between the data variable and the geographic region at at least one prior point in time; determining if the trend in the relationship is irregular within a predetermined threshold, generating an alert.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases, as well as the causes and effects of disease. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

Population monitoring may be used to monitor the spread of existing disease, the occurrence of new disease, or to determine if specific disease rates are changing. However, this information may be hard to monitor and organize for numerous reasons, which may range from a lack of personnel, inadequate communication among hospitals, to inadequate data collection and analysis tools.

The present systems and methods address this problem by aggregating clinical information using cloud-based data analysis of patient data. This data can come from hospitals, clinics, field researchers, and others. It may then be analyzed by machine learning, computer vision, natural language processing, and statistical algorithms to perform real-time monitoring and forecasting of health patterns at multiple geographic specificity levels. By centralizing the information pertaining to population disease rates, epidemiologists may identify trends sooner, so mitigation efforts may be put in place more quickly. Secondly, the utilization of AI to scan and diagnose pathology images from pathology slides removes possibility of human error in diagnosis or treatment in this process.

The process of using computers to assist in population monitoring may help in monitoring and organizing information pertaining to population health monitoring. A primary embodiment of the present disclosure involves aggregating information from sources that may potentially be located throughout the world. Machine learning may help to organize and find relationships within the provided information. Machine learning may also predict future relationships between selected variables, to estimate future rates of a disease or other health variable within a geographic region.

The below embodiments describe various machine learning algorithm training methods and implementations. These embodiments are merely exemplary. Any training methodologies could be used to train a machine learning model and/or system for the specific purpose of detecting external contaminants in a pathology slide. Below, some exemplary terms are described.

An input health variable may comprise a disease or other health related factor (e.g., cholesterol level, vitamin D, pathogens, cancers, etc.), as well as an input diagnostic slide. A training dataset may include a set of whole slide images (WSI) and/or additional diagnostic data from a set of cases used for training the machine learning (ML) algorithm. A validation dataset may include a set of WSIs and/or additional diagnostic data from a set of cases used for validating the generalizability of the ML algorithm. A set of labels may be used for each instance in the training data that contain information that an algorithm is being trained to predict (e.g., what disease is being monitored, etc.). A convolutional neural network (CNN) may refer to an architecture that may be built that can scan over the pathology slide. One embodiment may include training this CNN, using the training labels, to make one prediction per pathology slide about whether a disease is present. A CNN+Aggregator may refer to an architecture that may be built to incorporate information from a CNN that is executed over multiple localized regions of a pathology slide. One embodiment may include training this CNN, using the training labels, to make predictions for each region in the pathology slide about the likelihood that a disease is present in a specimen or scanned region. In some embodiments, a second model may take individual predictions over tissue/specimen/image regions as inputs and predict the likelihood that the pathology slide may contain a disease. Model Uncertainty may refer to a machine learning model that may be trained to predict any parameter about, or related to, a pathology slide, e.g., detection of the presence of a disease. The level of uncertainty the machine learning model has about specific predictions could be computed using a variety of methods, e.g., identifying an ambiguous range of the probability values such as those close to the threshold, using out-of-distribution techniques (Out-of-Distribution detector for Neural Networks (ODIN), tempered mix-up, Mahalanobis distance on the embedding space), etc. This uncertainty could be used to estimate the likelihood a slide may contain a disease.

According to one embodiment, a machine learning model may be trained to predict the relationship between a plurality of selected health or data variables in a geographic region, or in a selected sub-image of the geographic region. The output prediction from this model may then be used to determine whether to continue monitoring the health of the population.

Figure 1A:
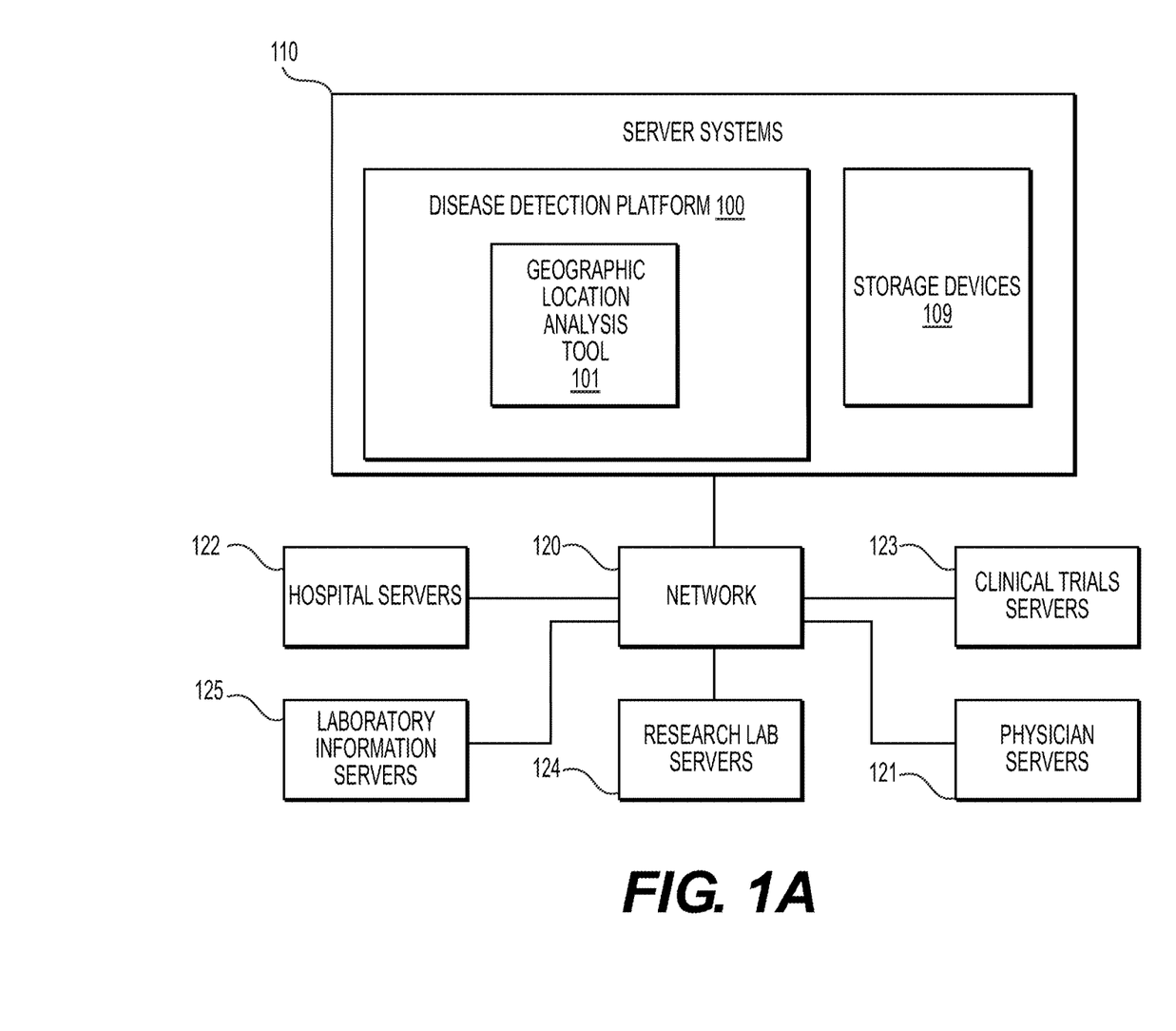
FIG. 1A illustrates an exemplary block diagram of a system and network for monitoring a population health, according to an exemplary embodiment of the present disclosure.

FIG. 1A illustrates an exemplary block diagram of a system and network for determining a relationship between a health variable or data variable and a geographic region, using machine learning, according to an exemplary embodiment of the present disclosure.

Specifically, FIG. 1A illustrates an electronic network 120 that may be connected to servers at hospitals, laboratories and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a disease detection platform 100, which includes a geographic location analysis tool 101 for determining specimen property or image property information pertaining to digital pathology image(s), and using machine learning to determine whether a disease or infectious agent is present, according to an exemplary embodiment of the present disclosure. The geographic location analysis tool 101 may also predict future relationships.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

Figure 1B:
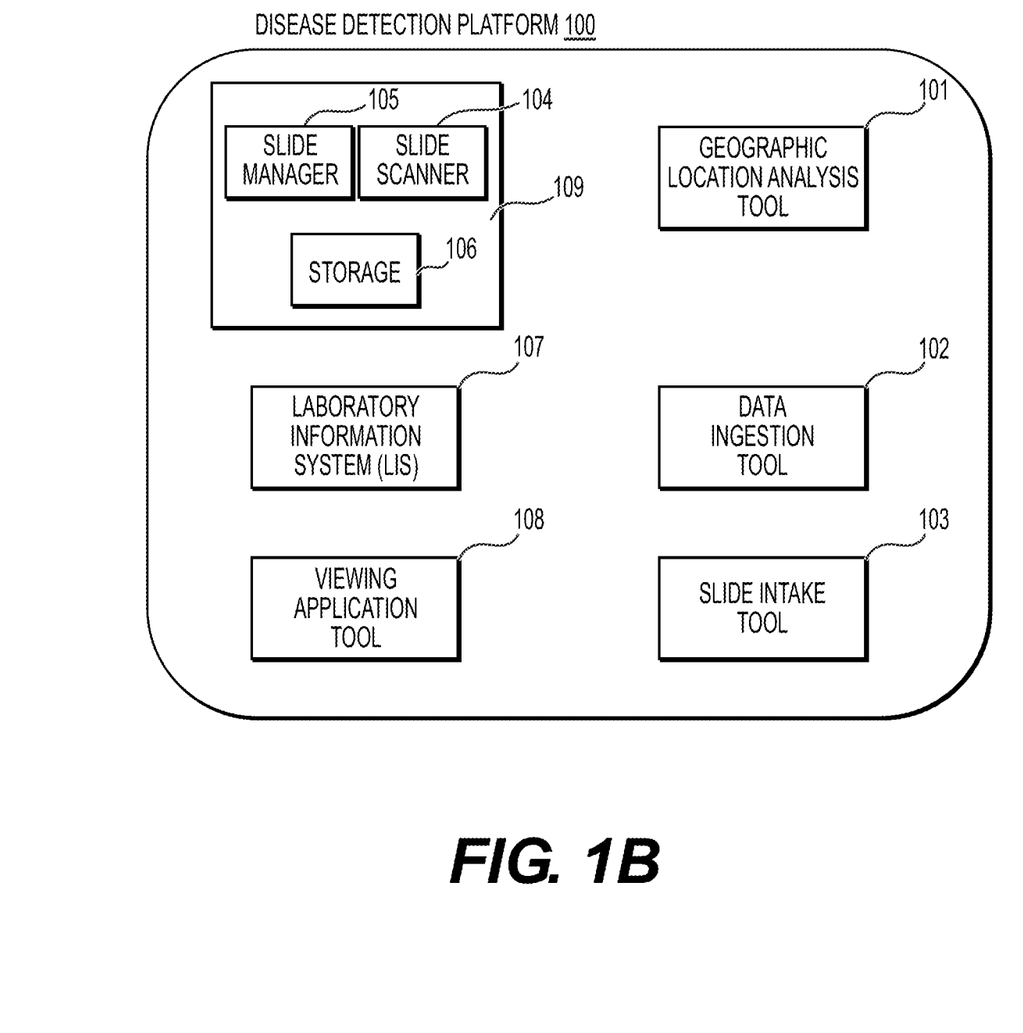
FIG. 1B illustrates an exemplary block diagram of a disease detection platform, according to an exemplary embodiment of the present disclosure.

FIG. 1B illustrates an exemplary block diagram of a disease detection platform 100 for determining specimen property or image property information pertaining to digital pathology image(s), using machine learning. The disease detection platform 100 may include a geographic location analysis tool 101, a data ingestion tool 102, a slide intake tool 103, a slide scanner 104, a slide manager 105, a storage 106, a laboratory information system 107 and a viewing application tool 108.

The geographic location analysis tool 101, as described below, refers to a process and system for determining data variable property or health variable property information pertaining to digital pathology image(s). Machine learning may be used to classify an image, according to an exemplary embodiment. The geographic location analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The geographic location analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the geographic location analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
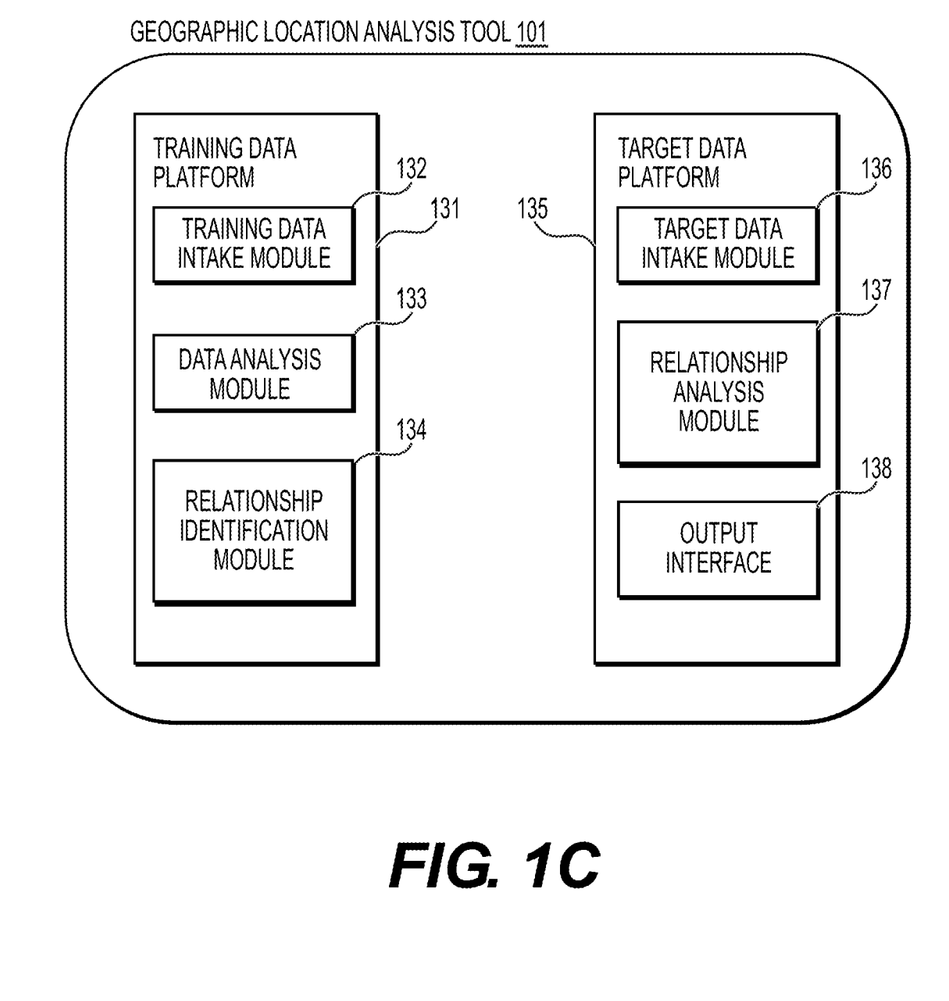
FIG. 1C illustrates an exemplary block diagram of a geographic location analysis tool, according to an exemplary embodiment of the present disclosure.

FIG. 1C illustrates an exemplary block diagram of a geographic location analysis tool 101, according to an exemplary embodiment of the present disclosure. The geographic location analysis tool 101 may include a training data platform 131 and/or a target data platform 135.

According to one embodiment, the training data platform 131 may include a training data intake module 132, a data analysis module 133, and a relationship identification module 134.

The training data platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training data intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify quality control (QC) issues (e.g., imperfections) for the training datasets at a global or local level that may greatly affect the usability of a dataset. For example, the quality score determiner module may use information about an entire dataset, e.g., the dataset type, the overall quality of the cut of the specimen, the overall quality of the dataset itself, or pathology slide characteristics, and determine an overall quality score for the dataset. The relationship identification module 134 may analyze health variables and/or data variables and determine whether a determined relationship has an irregular trend. It is useful to identify whether a relationship has an irregular trend, as trends may be used for future relationship predictions, and may trigger an alert to a user.

According to one embodiment, the target data platform 135 may include a target data intake module 136, a relationship analysis module 137, and an output interface 138. The target data platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target data intake module 136 may receive a target dataset corresponding to a target health variable or a data variable. The relationship analysis module 137 may apply the machine learning model to the target dataset to determine a characteristic of the target health variable or a data variable. For example, the relationship analysis module 137 may detect a trend of the target relationship. The relationship analysis module 137 may also apply the machine learning model to the target dataset to determine a quality score for the target dataset. Further, the relationship analysis module 137 may apply the machine learning model to the target dataset to determine whether the target health variable or a data variable is present in a determined relationship.

The output interface 138 may be used to output information about the target data and the determined relationship. (e.g., to a screen, monitor, storage device, web browser, etc.).

Figure 2A:
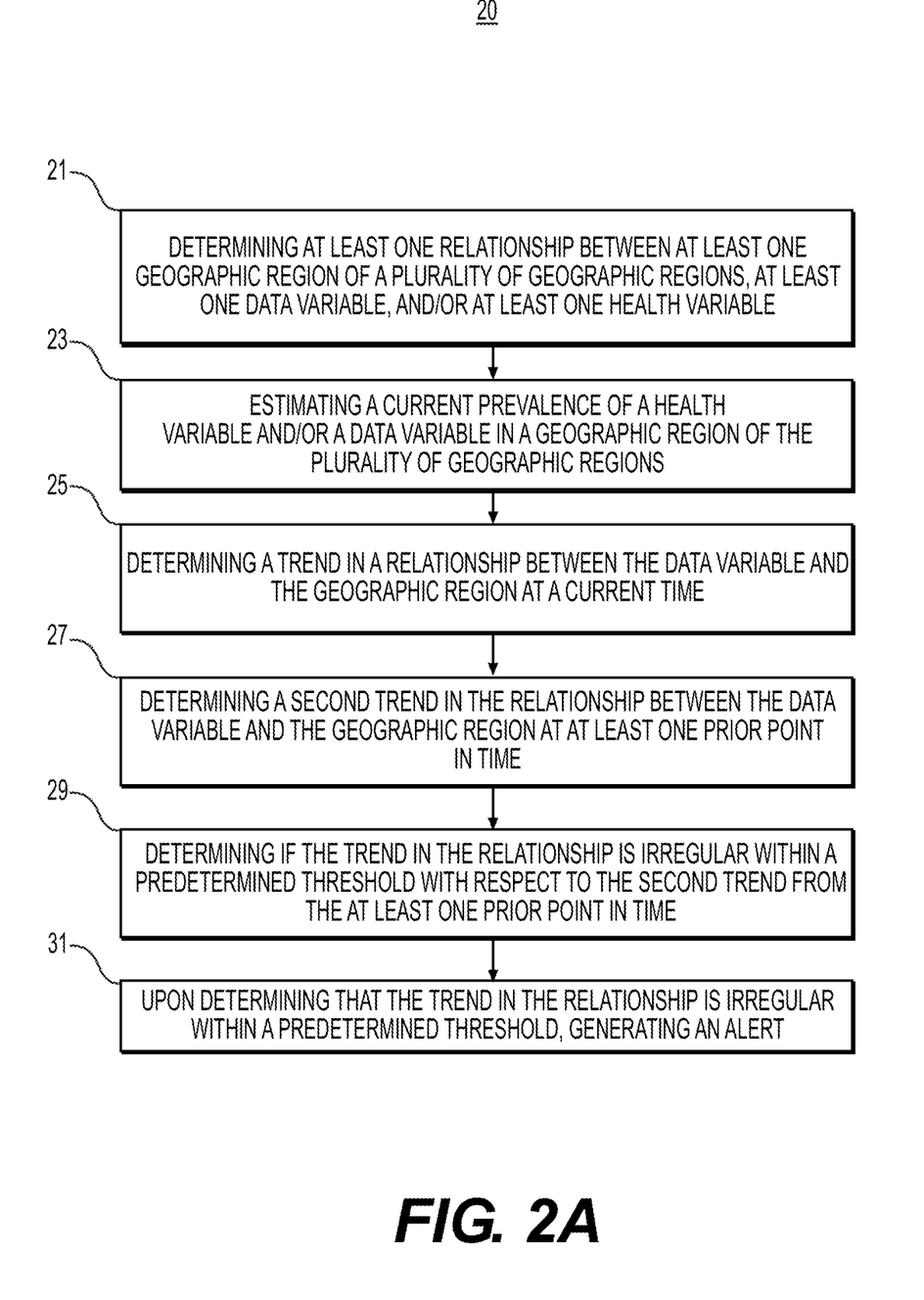
FIG. 2A is a flowchart illustrating an exemplary method for monitoring population health using machine learning, according to an exemplary embodiment of the present disclosure.

FIG. 2A is a flowchart illustrating an exemplary method for monitoring population health, using machine learning, according to an exemplary embodiment of the present disclosure. For example, an exemplary method 20 (e.g., steps 21-31) may be performed by geographic location analysis tool 101 automatically or in response to a request from a user.

According to one embodiment, the exemplary method 20 for monitoring a population health may include one or more of the following steps. In step 21, the method may include determining at least one relationship between at least one geographic region of a plurality of geographic regions, at least one data variable, and/or at least one health variable. For example, a health variable may comprise a disease or other health-related factor (e.g., cholesterol level, vitamin D level, pathogens, cancers, etc.), and a data variable may comprise an attribute of an individual (e.g., age, race, ethnicity, gender, income level, BMI, etc.). The health variable, data variable, and/or geographic region may be received from any one or any combination of the server systems 110, physician servers 121, hospital servers 122, clinical trial servers 123, research lab servers 124, and/or laboratory information systems 125.

In step 23, the method may include estimating the current prevalence of a data variable in a geographic region of the plurality of geographic regions. The geographic region may comprise a specific city, a county, a state, nationally, globally, etc.

In step 25, the method may include determining a trend in a relationship between the data variable and the geographic region at a current time. The trend may be determined via many means, e.g., a correlation machine learning method, geographic visual overlay, etc. For clarity, the trend may be determined between a geographic region(s) and a data variable(s), a geographic region(s) and health variables, or data variables and health variables within a geographic region.

In step 27, the method may include determining a second trend in the relationship between the data variable and the geographic region at at least one prior point in time.

In step 29, the method may include determining if the trend in the relationship is irregular within a predetermined threshold with respect to the second trend from the at least one prior point in time.

In step 31, the method may include, upon determining that the trend in the relationship is irregular within a predetermined threshold, generating an alert. This alert may comprise a visual display, a sound, or any other suitable alarm. The alert may be triggered if there is any irregularity detected in the determined relationship associated with the trend or the second trend of the determined relationship between the same variables within the same geographic region associated with a previous point in time.

Figure 2B:
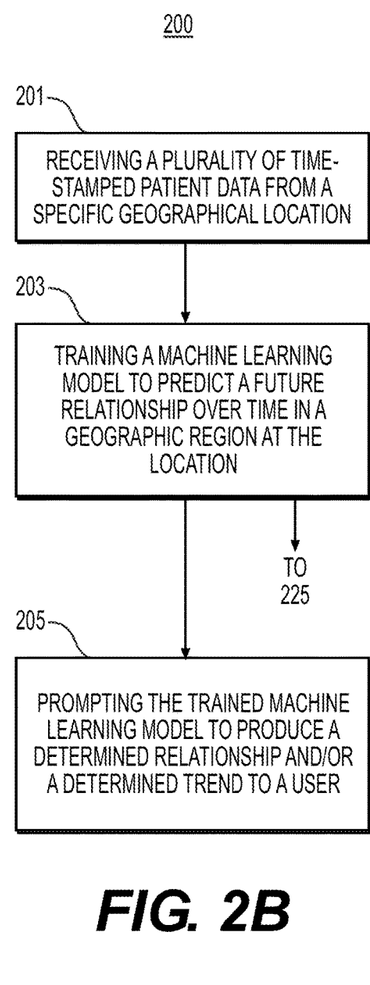
FIG. 2B is a flowchart illustrating an exemplary method of training a machine learning model to monitor a population health, according to an exemplary embodiment of the present disclosure.

FIG. 2B is a flowchart illustrating an exemplary method of applying a machine learning model to output a determined relationship between a health variable(s), a data variable(s), and/or a geographic region(s), according to an exemplary embodiment of the present disclosure. For example, an exemplary method 200 (e.g., steps 201-205) may be performed by a geographic location analysis tool 101 automatically or in response to a request from a user.

According to one embodiment, the exemplary method 200 for determining a relationship between variables and geographic region may include one or more of the following steps. In a step 201, the method may include receiving a plurality of time-stamped patient data from a specific geographical location. Patient data may include, but is not limited to, digital images of a pathology specimen (e.g., histology, cytology, etc.), genetic data, pathogenic data, clinical notes, health variables and/or data variables for the patient, test results, MRI scans, CT scans, pathology images, etc. Data may be received via networking or some other means. Patient data may be stored into a digital storage device, such as a hard drive, a network drive, a cloud storage, a RAM, etc.

In a step 203, the method may include training a machine learning model to predict a future relationship over time in a geographic region at the specific location. Additional information about the received geographic region or location may be included (e.g., context regarding environmental factors, current disease rates, information from neighboring geographical regions, past historical trends, etc.). The training algorithm may be implemented in a number of ways, including but not limited to, a convolutional neural network; a graph convolutional network, e.g., a node could be a feature associated with a geographic region; an autoregressive model; a recurrent neural network; and/or a capsule network.

In a step 205, the method may include prompting the trained machine learning model to produce a determined relationship and/or a determined trend to a user. The output may be sent to storage in an electronic storage device such as a hard disk, network drive, cloud, memory, etc., and/or transmitted to another location or user.

Figure 2C:
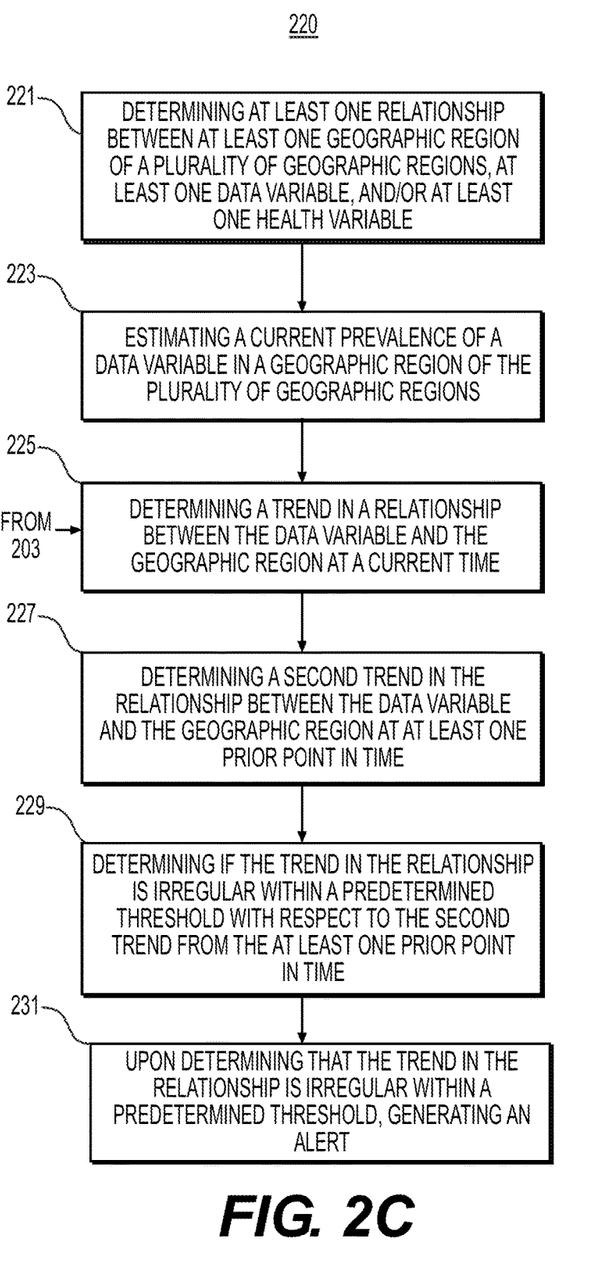
FIG. 2C is a flowchart illustrating an exemplary method for monitoring population health, using machine learning, according to an exemplary embodiment of the present disclosure.

FIG. 2C is a flowchart illustrating an exemplary method 220 for monitoring population health using machine learning, according to an exemplary embodiment of the present disclosure. For example, an exemplary method 220 (e.g. steps 221-231) may be performed by geographic location analysis tool 101 automatically or in response to a request from a user.

According to one embodiment, the exemplary method 220 for monitoring population health using machine learning may include one or more of the following steps. In a step 221, the method may include determining at least one relationship between at least one geographic region of a plurality of geographic regions, at least one data variable, and/or at least one health variable. For example, a particular health variable may comprise a disease or other health related factor (e.g., cholesterol level, vitamin D level, pathogens, cancers, etc.), and a particular data variable may comprise an attribute of an individual (e.g., race, ethnicity, gender, income level, BMI, etc.). The particular health variable, particular data variable, and/or geographic region may be received from any one or any combination of the server systems 110, physician servers 121, hospital servers 122, clinical trial servers 123, research lab servers 124, and/or laboratory information systems 125.

In a step 223, the method may include estimating the current prevalence of a data variable in a geographic region of the plurality of geographic regions. The geographic region may comprise a specific city, a county, a state, nationally, globally, etc. If a geographic region was received by the geographic location analysis tool 101, the estimation may be limited to the specified geographic region.

In a step 225, the method may include determining trend in a relationship between the data variable and the geographic region at a current time. The trend may be determined via many means, e.g., a correlation machine learning method, geographic visual overlay, etc. For clarity, the trend may be determined between a geographic region(s) and a data variable(s), a geographic region(s) and health variables, or data variables and health variables within a geographic region.

In a step 227, method may include determining a second trend in the relationship between the data variable and the geographic region at at least one prior point in time.

In a step 229, the method may include determining if the trend in the relationship is irregular within a predetermined threshold with respect to the second trend from the at least one prior point in time. An irregularity may comprise a mismatch between variables, a sudden upward or downward trend in a geographic region for a specific health or data variable, or other user-defined irregularity.

In a step 231, the method may include, upon determining that the trend in the relationship is irregular within a predetermined threshold, generating an alert. This alert may comprise a visual display, a sound, or any other suitable alarm. The alert may be triggered if there is any irregularity detected in the determined relationship associated with the timing of the received query and relationship between the same variables within the same geographic region associated with a previous point in time. Alternatively, the alert may comprise a data log entry.

Cancer rates vary across geographic regions for a wide variety of reasons, which may include local dietary trends, infectious agents, and environmental factors (e.g., pesticide usage in an agricultural region, various forms of air pollution, etc.). Embodiments of the present disclosure may help gain insight into the cause of this variation in cancer rates and to predict future rates among populations.

Figures 3A, 3B:
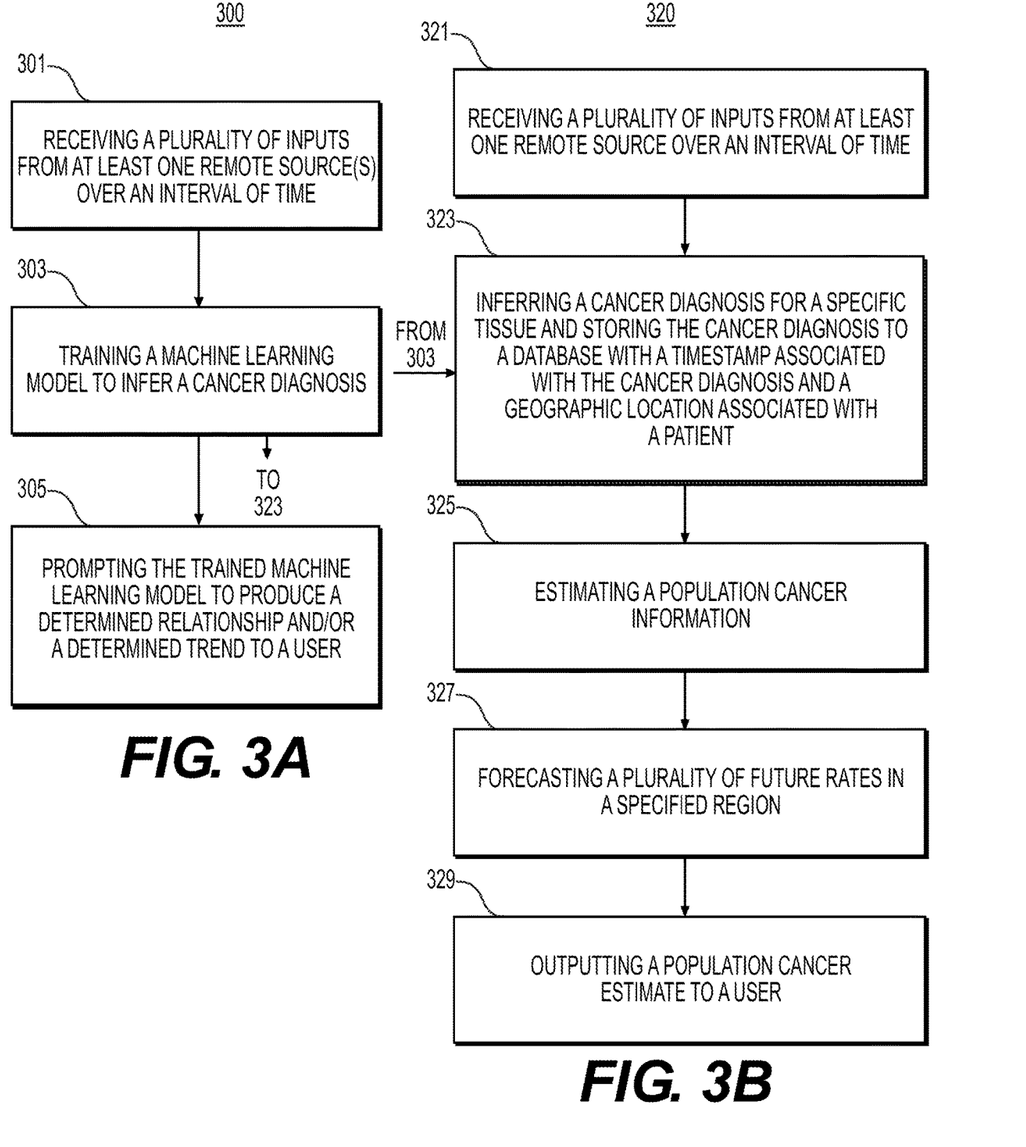
FIG. 3A is a flowchart illustrating an exemplary method of applying a machine learning model to produce a determined relationship and/or determined trend to a user, according to an exemplary embodiment.
FIG. 3B is a flowchart illustrating an exemplary method of estimating current cancer rates and predicting future cancer rates in one or more geographic locations, according to an exemplary embodiment of the present disclosure.

FIG. 3A is a flowchart illustrating an exemplary method of applying a machine learning model to produce a determined relationship and/or determined trend to a user, according to an exemplary embodiment. For example, an exemplary method 300 (e.g., steps 301-305) may be performed by geographic location analysis tool 101 automatically or in response from a user.

According to an embodiment, the exemplary method 300 for applying a machine learning to determine a population cancer rate may include one or more of the following steps. In a step 301, the method may include receiving a plurality of inputs from at least one remote source(s) over an interval of time. Inputs may include digital images of pathology specimens (e.g., histology, cytology, etc.), synoptic reports from healthcare providers, etc.

In a step 303, the method may include training a machine learning model to infer cancer diagnosis. Training a machine learning model may comprise using a machine learning model applied to the digital pathology, a natural language processing method, or by direct input from a remote source providing synoptic information.

In a step 305, the method may include prompting the trained machine learning model to produce a determined relationship and/or a determined trend to a user FIG. 3B is a flowchart illustrating an exemplary method of using the trained machine learning model to output a population cancer estimate to a user. For example, an exemplary method 320 (e.g., 321-329) may be performed by geographic location analysis tool 101 automatically or in response from a user.

According to an embodiment, the exemplary method 320 for using a machine learning model to estimate a population cancer rate may include one or more of the following steps. In a step 321, the method may include receiving a plurality of inputs from at least one remote source over an interval of time. The plurality of inputs may comprise digital images of pathology specimens (e.g., histology, cytology, etc.), synoptic reports from healthcare providers, etc. It may also include environmental variables of that geographic region such as food, water and air pollutants like pesticides, lead, car emissions, chemicals from factories, dust, pollen, mold spores, plastic micro-particles, etc. It may also include information about health trends in the population of that region or from the patients the pathology specimens were taken from such as dietary trends, exercise rates, smoking rates, prevalence of certain viruses (such as HPV), etc. At least one remote source for this information may comprise hospitals, laboratories, insurance providers, governments, public statistics, news organizations, publications and publicly available datasets.

In a step 323, the method may include inferring a cancer diagnosis for a specific tissue and storing the cancer diagnosis to a database with a timestamp associated with the cancer diagnosis and a geographic location associated with a patient. This step may be optional, as the method may output a population cancer estimate without inferring a cancer diagnosis for a specific tissue. The cancer diagnosis may be inferred using machine learning models applied to the digital pathology images, inferred using natural language processing from clinician notes, input directly from a remote source providing synoptic information, etc.

In a step 325, the method may include estimating a population cancer estimate. Estimating the current rate in a user specified geographic location may include specifying by the user by querying a database and specifying the region to be queried.

In a step 327, the method may include forecasting a plurality of future rates in a specified region. This step may be optional, as the method may output a population cancer rate without a predicted future rate in a specific geographic region. Future rates may be predicted by continually updating a statistical or machine learning algorithm to the data, e.g., a recurrent network, graph convolutional network where nodes represent feature vectors at a specific geographic location and edges are neighboring geographical regions, recurrent graph convolutional networks, various autoregressive models, etc. Inputs may include a geographical location with associated contextual feature vectors (e.g., pesticide usage, air pollution levels, etc.), and the output is a future cancer rate.

In a step 329, the method may include outputting a population cancer estimate to a user. The user may receive this estimate on a display, or the estimate may be stored in an electronic storage device such as a hard disk, a network drive, a cloud, a memory, etc. Additionally, outputting the estimate may comprise transmitting the estimate to another location or another user.

Figure 4A:
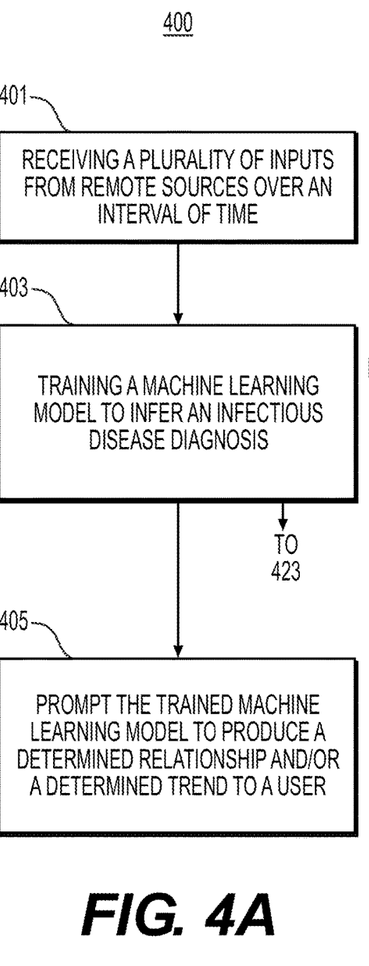
FIG. 4A is a flowchart illustrating an exemplary method of applying a machine learning model to produce a determined relationship and/or a determined trend of infectious disease in one or more geographic regions, according to an exemplary embodiment of the present disclosure.

FIG. 4A is a flowchart illustrating an exemplary method of applying a machine learning model to produce a determined relationship and/or a determined trend of infectious disease rates in one or more geographic regions to a user, according to an exemplary embodiment. For example, an exemplary method 400 (e.g., steps 401-405) may be performed by geographic location analysis tool 101 automatically or in response from a user.

According to one embodiment, the exemplary method 400 for applying a machine learning model may include one or more of the following steps. In step 401, the method may include receiving a plurality of inputs from at least one remote source(s) over an interval of time. Inputs may include digital images of pathology specimens (e.g., histology, cytology, etc.), synoptic reports from healthcare providers, etc.

In a step 403, the method may include training a machine learning model to infer infectious disease diagnosis. Training a machine learning model may comprise using a machine learning model applied to the digital pathology, a natural language processing method, or by direct input from a remote source providing synoptic information.

In a step 405, the method may include prompting the trained machine learning model to produce a determined relationship and/or a determined trend to a user.

Figure 4B:
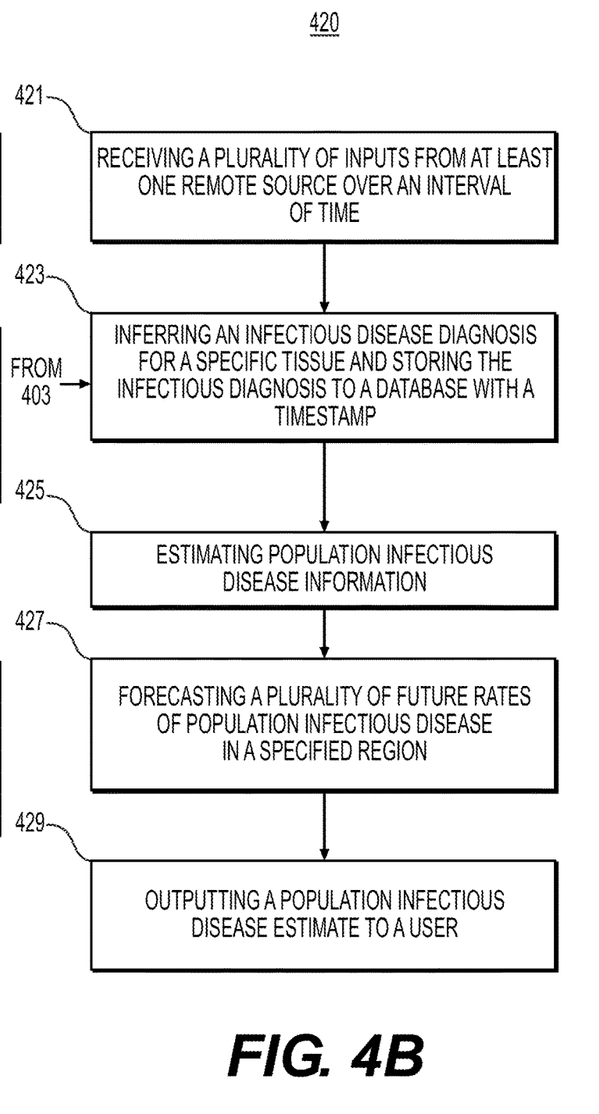
FIG. 4B is a flowchart illustrating an exemplary method of detecting and predicting trends of infectious disease in one or more geographic locations, according to an exemplary embodiment of the present disclosure.

FIG. 4B is a flowchart illustrating an exemplary method of using a machine learning model to produce a population infectious disease estimate to a user. For example, an exemplary method 420 (e.g., steps 421-429) may be performed by geographic location analysis tool 101 automatically or in response from a user.

According to an embodiment, the exemplary method 420 for using a machine learning model to produce a population infectious disease rate may include one or more of the following steps. In a step 421, the method may include the method may include receiving a plurality of inputs from at least one remote source over an interval of time. The plurality of inputs may comprise digital images of pathology specimens (e.g., histology, cytology, etc.), synoptic reports from healthcare providers, etc. It may also include environmental variables of that geographic region such as food, water and air pollutants like pesticides, lead, car emissions, chemicals from factories, dust, pollen, mold spores, plastic micro-particles, etc. It may also include information about health trends in the population of that region or from the patients the pathology specimens were taken from such as dietary trends, exercise rates, smoking rates, prevalence of certain viruses (such as HPV), etc. At least one remote source for this information may comprise hospitals, laboratories, insurance providers, governments, public statistics, news organizations, publications and publicly available datasets.

In a step 423, the method may include inferring an infectious disease diagnosis for a specific tissue and storing the infectious disease diagnosis to a database with a timestamp associated with the cancer diagnosis and a geographic location associated with a patient. The infectious disease diagnosis may be inferred using machine learning models applied to the digital pathology images, inferred using natural language processing from clinician notes, input directly from a remote source providing synoptic information, etc.

In a step 425, the method may include estimating a population infectious disease estimate. Estimating the current rate in a user specified geographic location may include specifying by the user by querying a database and specifying the region to be queried.

In a step 427, the method may include forecasting a plurality of future rates in a specified region. Future rates may be predicted by continually updating a statistical or machine learning algorithm to the data, e.g., a recurrent network, graph convolutional network where nodes represent feature vectors at a specific geographic location and edges are neighboring geographical regions, recurrent graph convolutional networks, various autoregressive models, etc. Inputs may include a geographical location with associated contextual feature vectors (e.g., pesticide usage, air pollution levels, etc.), and the output is a future infectious disease rate.

In a step 429, the method may include outputting a population infectious disease estimate to a user. The user may receive this estimate on a display, or the estimate may be stored in an electronic storage device such as a hard disk, a network drive, a cloud, a memory, etc. Additionally, outputting the estimate may comprise transmitting the estimate to another location or another user.

Figure 5A:
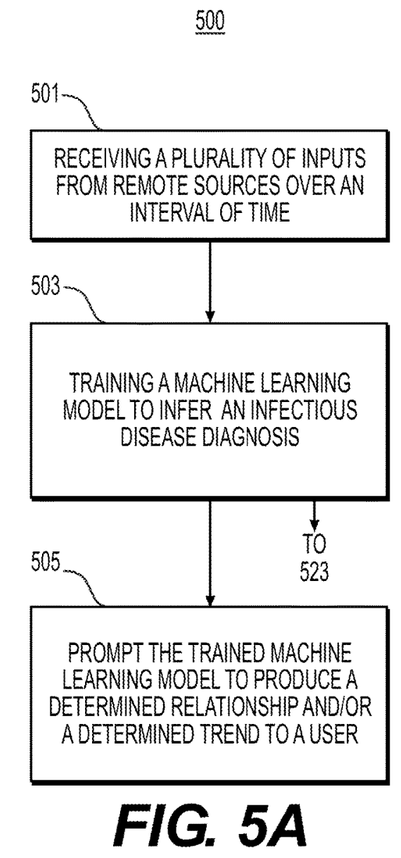
FIG. 5A is a flowchart illustrating an exemplary method of applying a machine learning model to produce a determined relationship and/or a determined trend of at least one health-related factor in a geographic region, according to an exemplary embodiment of the present disclosure.

FIG. 5A is a flowchart illustrating an exemplary method of training a machine learning model to produce a model of population health to a user. For example, an exemplary method 500 (e.g., steps 501-505) may be performed by geographic location analysis tool 101 automatically or in response from a user.

According to an embodiment, the exemplary method 500 for using a machine learning model to produce a model of population health to a user may include one or more of the following steps. In a step 501, the method may include receiving a plurality of inputs from at least one remote source(s) over an interval of time. Inputs may include digital images of pathology specimens (e.g., histology, cytology, etc.), synoptic reports from healthcare providers, etc.

In a step 503, the method may include training a machine learning model to infer infectious disease diagnosis. Training a machine learning model may comprise using a machine learning model applied to the digital pathology, a natural language processing method, or by direct input from a remote source providing synoptic information.

In a step 505, the method may include prompting the trained machine learning model to produce a determined relationship and/or a determined trend to a user.

Figure 5B:
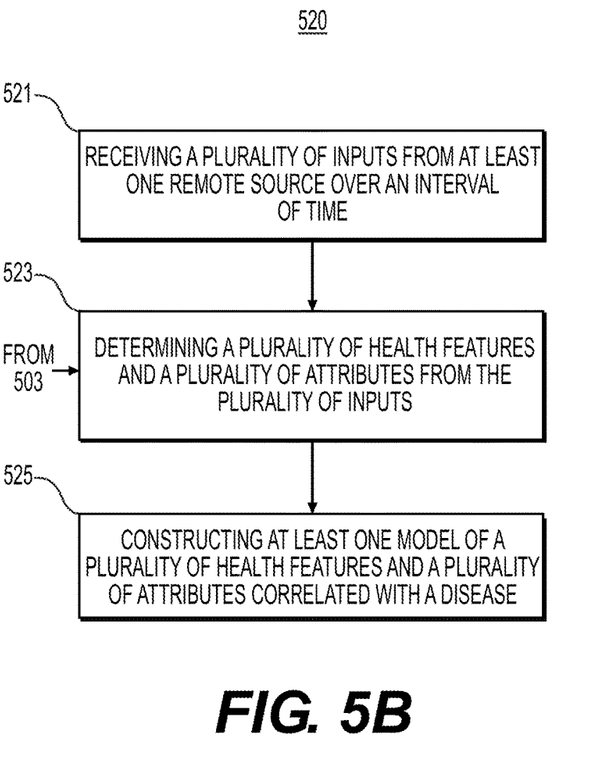
FIG. 5B is a flowchart illustrating an exemplary method of detecting and predicting trends of at least one health-related factor in a geographic region, according to an exemplary embodiment of the present disclosure.

FIG. 5B is a flowchart illustrating an exemplary method of using a machine learning model to produce a model of population health to a user. For example, an exemplary method 520 (e.g., steps 521-525) may be performed by geographic location analysis tool 101 automatically or in response from a user.

According to an embodiment, the exemplary method 520 (e.g., steps 521-525) for using a machine learning model to produce a model of population health to a user may include one or more of the following steps. In a step 521, the method may include receiving a plurality of inputs from at least one remote source over an interval of time. The plurality of inputs may comprise digital images of pathology specimens (e.g., histology, cytology, etc.), synoptic reports from healthcare providers, etc. It may also include environmental variables of that geographic region such as food, water and air pollutants like pesticides, lead, car emissions, chemicals from factories, dust, pollen, mold spores, plastic micro-particles, etc. It may also include information about health trends in the population of that region or from the patients the pathology specimens were taken from such as dietary trends, exercise rates, smoking rates, prevalence of certain viruses (such as HPV), etc. At least one remote source for this information may comprise hospitals, laboratories, insurance providers, governments, public statistics, news organizations, publications and publicly available datasets.

In a step 523, the method may include determining health features and attributes from the plurality of inputs.

In a step 525, the method may include constructing at least one model of a plurality of various attributes correlated with a disease.

Figure 6:
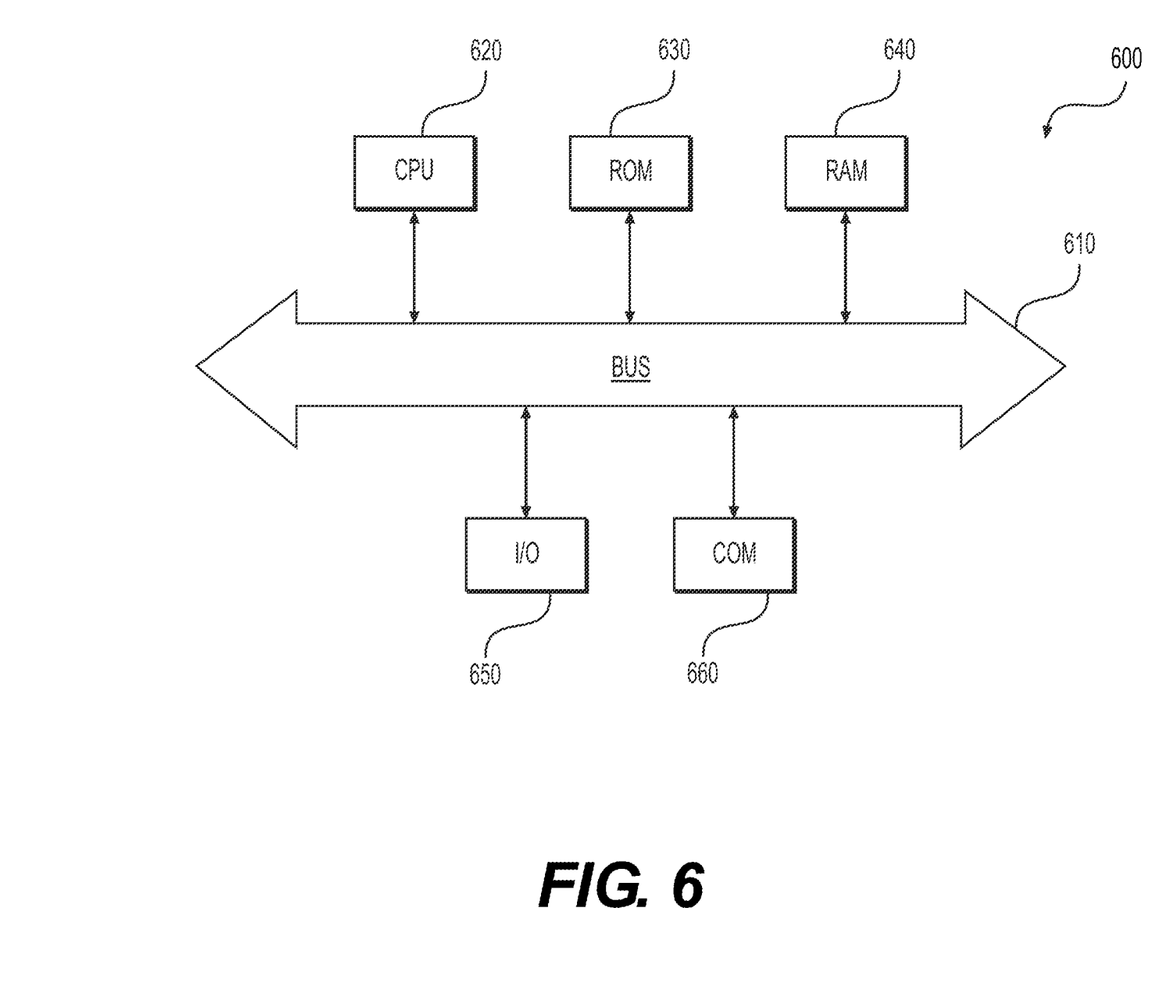
FIG. 6 illustrates an example system that may execute techniques presented herein.

As shown in FIG. 6, device 600 may include a central processing unit (CPU) 620. CPU 620 may be any type of processor device including, for example, any type of special purpose or a general-purpose microprocessor device. As will be appreciated by persons skilled in the relevant art, CPU 620 also may be a single processor in a multi-core/multi-processor system, such system operating alone, or in a cluster of computing devices operating in a cluster or server farm. CPU 620 may be connected to a data communication infrastructure 610, for example a bus, message queue, network, or multi-core message-passing scheme.

Device 600 may also include a main memory 640, for example, random access memory (RAM), and also may include a secondary memory 630. Secondary memory 630, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 630 may include similar means for allowing computer programs or other instructions to be loaded into device 600. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 600.

Device 600 also may include a communications interface ("COM") 660. Communications interface 660 allows software and data to be transferred between device 600 and external devices. Communications interface 660 may include a modem, a network interface (such as an Ethernet card), a communications port, a PCMCIA slot and card, or the like. Software and data transferred via communications interface 660 may be in the form of signals, which may be electronic, electromagnetic, optical or other signals capable of being received by communications interface 660. These signals may be provided to communications interface 660 via a communications path of device 600, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 600 may also include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for monitoring health of a patient population, the method comprising:
    determining, based on time-stamped patient data of the patient population, a relationship between at least one geographic region of a plurality of geographic regions associated with the patient population, at least one data variable, and at least one health variable of patients of the patient population;
    estimating a current prevalence of a data variable in the at least one geographic region of the plurality of geographic regions;
    determining a first trend in the relationship between the data variable and the geographic region at a current time;
    determining a second trend in the relationship of the first trend between the data variable and the geographic region at at least one prior point in time;
    determining if the first trend in the relationship is irregular within a predetermined threshold with respect to the second trend from the at least one prior point in time, the predetermined threshold being identified using a deep learning out-of-distribution technique, and the first trend being irregular as determined between at least one of a geographic region and a demographic variable, a geographic region and a health variable, and a data variable and a health variable within a geographic region; and
    upon determining that the first trend in the relationship is irregular within the predetermined threshold, generating an alert related to the patient population.

2. The computer-implemented method of claim 1, further comprising:
    receiving the time-stamped patient data from at least one of one or more physician servers, hospital servers, clinical trial servers, research lab servers, and/or laboratory information systems;
    generating an updated relationship between the at least one geographic region, the at least one data variable, and the at least one health variable based on the determined relationship, comprising:
    providing the at least one relationship to a machine learning model;
    applying the machine learning model to predict at least one future relationship over a time period in the at least one geographic region; and
    generating the updated relationship between the at least one geographic region, the at least one data variable, and the at least one health variable based on the at least one future relationship.

3. The computer-implemented method of claim 2, wherein the machine learning model comprises:
    a convolutional neural network; a graph convolutional network; an autoregressive model; a recurrent neural network; and/or a capsule network.

4. The computer-implemented method of claim 2, wherein applying the machine learning model to predict at least one future relationship over time period in the at least one geographic region comprises:
    inferring health related variables from the time-stamped patient data; and
    determining disease states and applying at least one natural language processing model to at least one clinic note to extract at least one relevant variable.

5. The computer-implemented method of claim 1, wherein the time-stamped patient data comprises at least one of a plurality of digital images of pathology specimens, genetic data, pathogenic data, and clinical notes.

6. The computer-implemented method of claim 4, further comprising:
    storing the time-stamped patient data into a digital storage device.

7. The computer-implemented method of claim 2, wherein applying a machine learning model to predict at least one future relationship over time in the at least one geographic region comprises using at least one of: a convolutional neural network; a graph convolution network; an autoregressive model; a recurrent neural network; and a capsule network.

8. The computer-implemented method of claim 1, wherein determining the at least one relationship between the at least one geographic region, at least one data variable, or at least one health variable comprises using correlation machine learning and/or geographic visual overlay.

9. The computer-implemented method of claim 1, wherein a query is received from a user for one of a particular health variable, a particular data variable.

10. The computer-implemented method of claim 1, wherein a trend is irregular if a variable mismatch is identified or if a sudden increase or a sudden decrease of a trend is detected.

11. A system for monitoring health of a patient population, the system comprising:
  at least one memory storing instructions; and
  at least one processor configured to execute the instructions to perform operations comprising:
    receiving a query for a particular health variable, a data variable, and a geographic region;
    estimating a current prevalence of a data variable in a geographic region;
    determining a first trend in a relationship of the patient population at a current time;
    determining a second trend in the relationship of the first trend between the data variable and the geographic region at at least one prior point in time;
    generating an alert, related to the patient population, if the first trend in the relationship is irregular within a predetermined threshold with respect to the second trend from the at least one prior point in time, the predetermined threshold being identified using a deep learning out-of-distribution technique, and the trend being irregular as determined between at least one of a geographic region and a demographic variable, a geographic region and a health variable, and a data variable and a health variable within a geographic region;
    training a machine learning model to predict future relationships over time in a geographic region; and
    determining, based on the predicted future relationships, whether to continue monitoring health of the patient population.

12. The system of claim 11, the operations further comprising:
  generating an updated relationship between the at least one geographic region, the at least one data variable, and the at least one health variable based on the relationship, comprising:
  providing the at updated relationship to a machine learning model;
  applying the machine learning model to predict at least one future relationship over a time period in the at least one geographic region; and
  generating the updated relationship between the at least one geographic region, the at least one data variable, and the at least one health variable based on the at least one future relationship.

13. The system of claim 12, wherein the machine learning model comprises:
  a convolutional neural network; a graph convolutional network, an autoregressive model, a recurrent neural network, and/or a capsule network.

14. The system of claim 12, wherein applying the machine learning model to predict the at least one future relationship over the time period in the at least one geographic region comprises:
  inferring health related variables from a time-stamped patient data; and
  determining disease states and applying at least one natural language processing model to at least one clinic note to extract at least one relevant variable.

15. The system of claim 14, wherein the time-stamped patient data comprises at least one of digital images of pathology specimens, genetic data, pathogenic data, and/or clinical notes.

16. The system of claim 14, the operations further comprising:
  storing the time-stamped patient data into a digital storage device.

17. The system of claim 12, wherein applying a machine learning model to predict at least one future relationship over time in the at least one geographic region comprises using at least one of: a convolutional neural network; a graph convolution network; an autoregressive model; a recurrent neural network; and a capsule network.

18. The system of claim 11, wherein determining the relationship between the at least one geographic region, at least one data variable, at least one health variable comprises using correlation machine learning and/or geographic visual overlay.

19. The system of claim 11, wherein a query is received from a user for one of a particular health variable, a particular data variable.

20. A non-transitory computer readable medium storing instructions that, when executed by a processor, cause the processor to perform a method for monitoring health of a patient population, the method comprising:
  receiving a query for a particular health variable, a data variable, and/or a geographic region;
  estimating a current prevalence of a data variable in a geographic region of the patient population;
  determining, based on time-stamped patient data of the patient population, a first trend in a relationship between at least one geographic region(s), at least one data variable(s), and at least one health variable(s);
  determining a second trend in the relationship of the first trend between the data variable and the geographic region at at least one prior point in time;
  generating an alert if the second trend is irregular within a predetermined threshold with respect to the second trend from the at least one prior point in time, the predetermined threshold being identified using a deep learning out-of-distribution technique, and the first trend being irregular as determined between at least one of a geographic region and a demographic variable, a geographic region and a health variable, and a data variable and a health variable within a geographic region;
  training a machine learning model to predict future relationships related to the patient population over time in the geographic region; and
  determining, based on the predicted future relationships, whether to continue monitoring health of the patient population.

* * * * *